(12) United States Patent
Nelson et al.

(10) Patent No.: US 6,358,383 B2
(45) Date of Patent: *Mar. 19, 2002

(54) EXHAUST CONSTITUENT SENSOR AND METHOD OF PACKAGING THE SAME

(75) Inventors: Charles Scott Nelson, Clio; James P. Vargo, Swartz Creek; John A. Horton, Clio, all of MI (US)

(73) Assignee: Delphi Technologies, Inc., Troy, MI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/276,334

(22) Filed: Mar. 25, 1999

(51) Int. Cl.$^7$ .............................................. G01N 27/407
(52) U.S. Cl. ...................................... 204/426; 204/428
(58) Field of Search ................................. 204/421–429

(56) References Cited

U.S. PATENT DOCUMENTS

| | | | | |
|---|---|---|---|---|
| 3,844,920 A | * | 10/1974 | Burgett et al. | 204/428 |
| 4,198,279 A | * | 4/1980 | Brown et al. | 204/428 |
| 4,732,663 A | * | 3/1988 | Kato et al. | 204/428 |
| 5,616,825 A | * | 4/1997 | Achey et al. | 204/426 |
| 5,942,092 A | * | 8/1999 | Weyl et al. | 204/428 |
| 6,083,371 A | * | 7/2000 | Weyl et al. | 204/428 |

OTHER PUBLICATIONS

Harkh's Chemical Dictionary, (1969), 4$^{th}$ ed., p. 710.*

* cited by examiner

*Primary Examiner*—T. Tung
(74) *Attorney, Agent, or Firm*—Vincent A. Cighosz

(57) ABSTRACT

In an exemplary embodiment, the present invention provides an exhaust constituent sensor comprising a planar sensing element securely held in place within a tubular shield by disposing a high temperature mat support between the tubular inner shield and the planar sensing element. The high temperature mat support comprises suitable mat material, e.g., ceramic fibers or metal mesh, and preferably, comprises silica fibers, alumina fibers, alumina fibers with vermiculite, or any other suitable mat material providing the desired support, strength, and thermal and electrical insulating properties described herein. It is within the scope of the invention that the high temperature mat support may be in the form of a fibrous material or a more rigid perform structure, wherein in both instances, the high temperature mat support is adapted to be disposed concentrically around the planar sensing element for secure packaging thereof.

23 Claims, 2 Drawing Sheets

EXHAUST CONSTITUENT SENSOR AND METHOD OF PACKAGING THE SAME

TECHNICAL FIELD

The present invention relates generally to planar sensors. More particularly, the present invention relates to a method of supporting and holding a planar sensing element of an exhaust constituent sensor in a robust simple package.

BACKGROUND OF THE INVENTION

Exhaust constituent sensors have been used for many years in automotive vehicles to sense the presence of constituents in exhaust gasses (e.g., oxygen, hydrocarbons, nitrous oxides) and to sense, for example, when an exhaust gas content switches from rich to lean or lean to rich. One known type of exhaust constituent sensor includes a flat plate exhaust sensor formed of various layers of ceramic and electrolyte materials laminated and sintered together with electrical connections placed between the layers in a known manner.

Because automotive exhaust constituent sensors are mounted to members of the vehicle exhaust flow system, the sensors must be durable, able to withstand vibration and jarring such as would occur during installation and normal vehicle operation and able to withstand shock from the occasional stone or other small road debris that may happen to be thrown at the sensor, for example, by the vehicle's tires.

Typically, great care is required when packaging and holding the flat plate sensing element within the outer housing (body) of the exhaust constituent sensor. The flat plate sensing element can be both difficult and expensive to package within the body of the exhaust constituent sensor since it generally has one dimension that is very thin and is usually made of a brittle material. For example, one method of protecting the planar sensing element is to encase and hold the planar sensing element in proper position within a glass tube which is itself bonded to a metal shield of the exhaust constituent sensor. This process is time consuming and is therefore expensive in terms of manufacturing costs. Consequently, great care and time consuming effort must be taken to prevent the planar sensing element from being damaged by exhaust, heat, impact, vibration, the environment, etc.

SUMMARY OF THE INVENTION

The present invention comprises exhaust constituent sensors and a method of manufacturing same, and more particularly relates to a method of supporting and holding a planar sensing element in a robust simple package. One embodiment comprises an exhaust constituent sensor, comprising a planar sensing element securely held in place within a tubular shield by disposing a high temperature mat support between the tubular shield and the planar sensing element. It being understood that the high temperature mat support of the present invention comprises mat materials which are designed to withstand the heat generated in a spark ignition environment.

The high temperature mat support positions and secures the planar sensing element within the tubular shield and also advantageously provides an exhaust gas barrier in the sensor so that exhaust gas is blocked from a central portion and an upper portion of the planar sensing element. The high temperature mat support filter provides an instrument to dissipate heat from the inside of the sensor. The dissipation of heat from the planar sensing element reduces the possibility that excessive heat contacts the electrical connection of the planar sensing element during operation.

Advantageously, this invention provides an exhaust constituent sensor having improved holding of the planar sensing element within a sensor housing which provides improved resistance to failures caused by exposures to exhaust, heat, impact, vibration, and other environmental hazards which adversely effect the performance of the exhaust constituent sensor. Furthermore, the sensor of the present invention greatly simplifies the overall process of packaging a planar sensing element within an exhaust constituent sensor and as a result reduces the associated costs of the process.

BRIEF DESCRIPTION OF THE DRAWINGS

The present invention will now be described by way of example with reference to the following Figures, which are meant to be exemplary, not limiting, and in which.

DETAILED DESCRIPTION OF THE INVENTION

Figure 1:
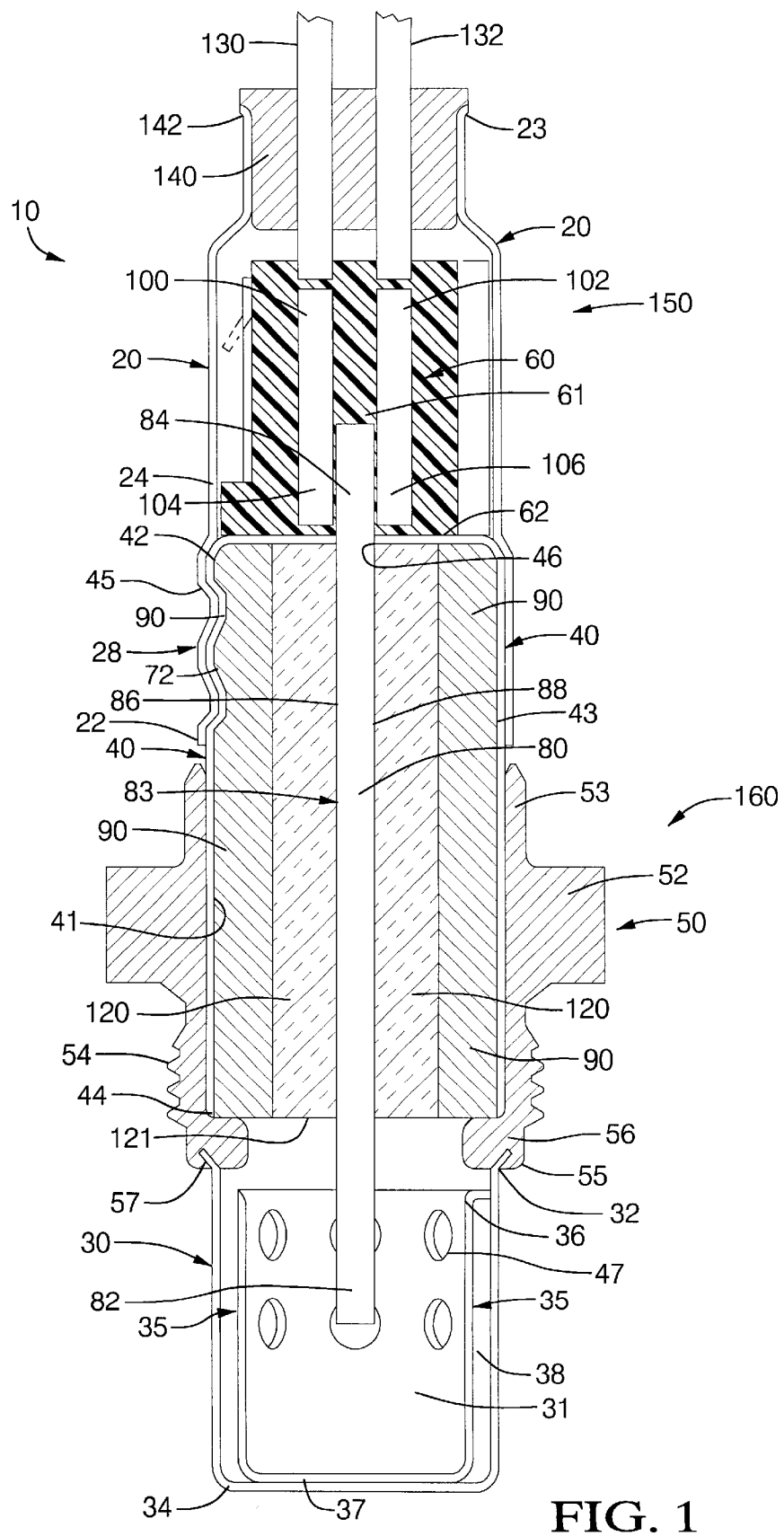
FIG. 1 is a cross-sectional side view of one embodiment of an exhaust constituent sensor embodying the present invention.

Referring now to FIG. 1, the example exhaust constituent sensor 10 shown includes a housing structure generally formed of an upper shield 20, a lower shield 30, an inner shield 40 and a shell 50. A terminal connector 60 and a portion of a planar sensing element 80 are disposed within upper shield 20. Planar sensing element 80 is an exhaust constituent sensing element of a known type with any conventional geometry, such as a generally flat elongated rectangular shape. At a first end 82 thereof, planar sensing element 80 includes an exhaust constituent-responsive structure fabricated into planar sensing element 80 in a known manner, preferably along with a heater (not shown) of a known type. At an opposite end 84 of planar sensing element 80, lower ends 104 and 106 of terminals 100 and 102, respectively, contact external pads (not shown) on end 84 to provide electrical connection between terminals 100 and 102 and planar sensing element 80. Ends 104 and 106 of terminals 100 and 102, respectively, are maintained against end 84 of planar sensing element 80 by a compressive force applied by disposing end 84 of planar sensing element 80 between lower ends 104 and 106. Preferably, terminals 100 and 102 comprise spring terminals, the use of which is in the art and the compressive force generated by disposing end 84 between spring terminals 100 and 102 securely maintains end 84 in electrical contact therewith.

The inner shield 40 has a partially closed first end 42 and an open second end 44 opposite first end 42. A centrally located annular opening 46 is provided at first end 42 and is sized to receive end 84 of planar sensing element 80. Disposed within inner shield 40 are a central portion 83 of planar sensing element 80, a pair of inner thermal insulating members 120, (e.g.)ceramic support members and a high temperature mat support 90. In accordance with the present invention, the pair of inner thermal insulating members 120 are provided for securely positioning and protecting planar sensing element 80 within exhaust constituent sensor 10, wherein first end 82 and second end 84 of planar sensing element 80 extend beyond the pair of inner thermal insulating members 120 when the pair of inner thermal insulating members 120 are disposed onto a first surface 86 and an opposing second surface 88 of the planar sensing element 80. In an exemplary embodiment, the pair of inner thermal insulating members 120 are semi-circular in shape and provide structural rigidity and protection to exhaust constituent sensor 10, and more specifically to planar sensing element 80 which is disposed therebetween. Example material for the pair of inner thermal insulating members 120 is steatite, rigid alumina, ceramic, or other suitable high temperature material providing the desired support, strength and thermal and electrical insulating properties described hereinbelow. As used herein, the term "high temperature material" refers to materials which are designed for use in a spark ignition engine environment, where temperatures range from about 300° C. to about 1000° C.

Disposed between the pair of inner thermal insulating members 120 and inner shield 40 is high temperature mat support 90 for further insulation and packaging of planar sensing element 80, wherein high temperature mat support 90 comprises a mat material designed for use in a spark ignition engine environment. More specifically, high temperature mat support 90 is formed of a mat material designed to withstand continuous exposure to temperatures on the order of about 300° C. to about 1000° C. (temperature range observed in spark ignition engine environment). High temperature mat support 90 extends from first end 42 to second end 44 of inner shield 40 so that high temperature mat support 90 is in contact with and abuts against an inner surface 41 of inner shield 40. High temperature mat support 90 provides the desired structural support to exhaust constituent sensor 10 by concentrically surrounding planar sensing element 80 and the pair of inner thermal insulating members 120 to thereby securely hold planar sensing element 80 in place. Furthermore, high temperature mat support 90 also acts as a thermal and gas barrier to inhibit access of excessive heat and exhaust gasses, respectively.

High temperature mat support 90 comprises mat materials designed to withstand the high temperatures observed in a spark ignition engine environment and in an exemplary embodiment, high temperature mat support 90 comprises a ceramic fibrous material or a metal mesh material. When a ceramic fibrous material is used, the orientation and size of the ceramic fibers are not critical to the practice of the present invention; however, the fibers are preferably orientated in a random fashion instead of a more ordered orientation of the fibers. In one preferred embodiment, high temperature mat support 90 comprises a mat material formed of ceramic fibers, including but not limited to silica fibers, alumina fibers, or mixtures thereof. Furthermore, vermiculite may be incorporated into the ceramic fibrous material as a component. As is known, vermiculite is a form of the mineral mica, and materials having vermiculite incorporated therein will slightly expand in volume when the materials are subjected to increases in temperature. More preferably, high temperature mat support 90 comprises a fibrous material formed of random alumina fibers and vermiculite. By incorporating vermiculite into the alumina fibrous material, high temperature mat support 90 will slightly expand when subjected to the high temperature environment of the exhaust system, resulting in high temperature mat support 90 expanding against inner surface 41 to provide a more effective support and gas barrier.

Exhaust gas is blocked from central portion 83 of planar sensing element 80 by the pair of inner thermal insulating members 120 and high temperature mat support 90 which prevent exhaust gasses from migrating within sensor 10 toward the electrical connection. Heat is dissipated from the pair of inner thermal insulating members 120 and planar sensing element 80 when the exhaust constituent sensor 10 is subjected to high temperatures due to the heat being drawn away therefrom by high temperature protective mat support 90 which conducts the heat therefrom to prevent excessive heat from contacting the electrical connection of planar sensing element 80.

In one form, high temperature mat support 90 comprises a flexible mat material, similar to a flexible fibrous blanket material which is easily disposed around the pair of inner thermal insulating members 120 and planar sensing element 80 by concentrically wrapping high temperature mat support 90 around at least a portion of the same so that the overall diameter of the inner components (planar sensing element 80, pair of inner thermal insulating members 120 and high temperature mat support 90) closely approximates the inner diameter of inner shield 40. Accordingly, when planar sensing element 80, the pair of inner thermal insulating members 120 and high temperature mat support 90 are disposed within inner shield 40, the components of sensor 10 are effectively and easily packaged within inner shield 40 resulting in planar sensing element 80 being securely held in place.

In the example shown in FIG. 1, a lower end 22 of the upper shield 20 extends to an upper portion 43 of high temperature mat support 90 and engages closed first end 42 of the inner shield 40 by a secure friction fit or other securing means known in the art, e.g., compressive forces exerted during assembly. In an exemplary embodiment, a first subassembly 150 comprises upper shield 20, a cable seal 140, and terminal connector 60, whereby upper shield 20 holds cable seal 140 and terminal connector 60 securely in place between upper shield 20. First subassembly 150 is securely coupled to a second subassembly 160 by inserting end 84 of planar sensing element 80 into an opening 61 located between terminals 100 and 102 until a first end 62 of terminal connector 60 seats against first closed end 42 of inner shield 40. Second subassembly 160 comprises inner shield 40 which is concentrically disposed around high temperature mat support 90, the pair of inner thermal insulating members 120 and planar sensing element 80. Alternatively, sensor 10 may be assembled without the use of subassemblies, whereby all individual components are properly positioned and secured during the assembly process.

Shell 50 includes a body portion 52 and a threaded portion 54 at a second end 55. Body portion 52 is shaped to accommodate a wrench or other tool for tightening threaded portion 54 into a mount welded to an exhaust pipe or other component of an exhaust flow system enabling a sensor chamber 31 located within lower shield 30 to be located within a flow of exhaust gasses to be measured. A first end 53 of shell 50 is disposed proximate lower end 22 of the upper shield 20 when shell 50 is securely disposed around inner shield 40 by means known in the art; and preferably, shell 50 is coupled to inner shield 40 by being crimped thereto during the assembly process, as described in more detail hereinafter. Accordingly, shell 50 holds inner shield 40 in compressive force engagement. Formed at second end 55 of shell 50 is a shoulder 56 for contacting open second end 44 of inner shield 40, whereby inner shield 40 and an end 121 of pair of inner thermal insulating members 120 rests against shoulder 56 when shell 50 is secured to inner shield 40 during assembly.

Formed at second end 55 of shell 50 is an annular recess 57 for receiving a flared open end 32 of the lower shield 30.

Flared open end 32 of lower shield 30 receives end 82 of planar sensing element 80, whereby end 82 is disposed within sensing chamber 31 to permit contact with and sensing of exhaust gas. Lower shield 30 has a closed end 34 opposite flared open end 32 of inner shield 30, wherein flared open end 32 is secured to second end 55 of shell 50 by disposing flared open end 32 into annular recess 57 and securing flared open end 32 therein by welding it in place or holding it in place by a secure friction fit.

Lower shield 30 defines sensing chamber 31 and disposed within lower shield 30 is an internal shield 35 which has an open end 36 for receiving planar sensing element 80 and a closed end 37 adjacent and parallel to closed end 34 of lower shield 30. Lower shield 30 and internal shield 35 form a plurality of vents 38 for allowing passage of exhaust gas in and out of sensing chamber 31 so that the gasses may be sensed by receptive first end 82 of planar sensing element 80. A plurality of openings 47 permits exhaust gas to flow into exhaust constituent sensor 10, and more specifically, exhaust gas flows through openings 47 and vents 38 into sensing chamber 31.

Figure 2:
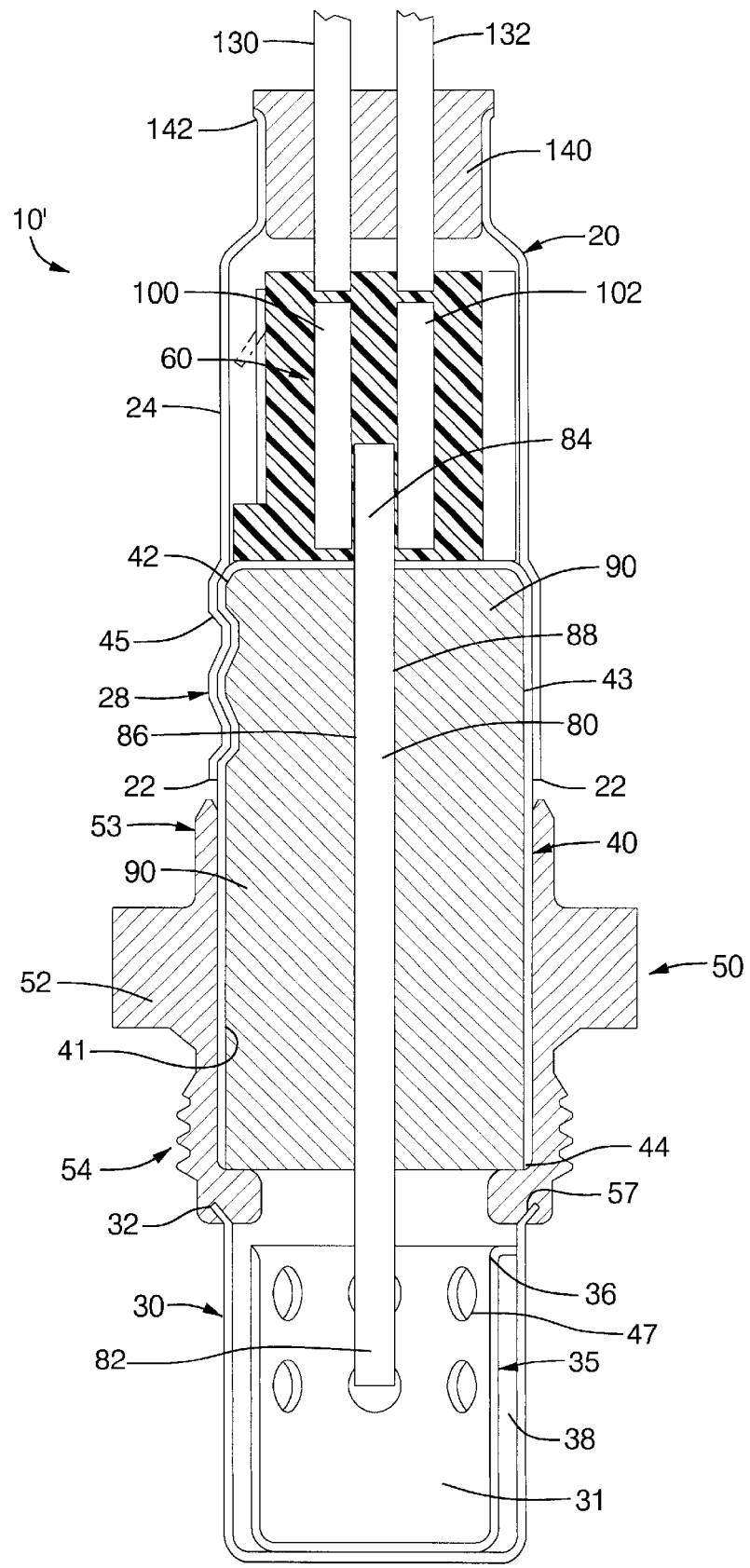
FIG. 2 is a cross-sectional side view of a second embodiment of the exhaust constituent sensor of the present invention.

The use of terminal connector 60 is known in the art and a suitable terminal connector 60 is also known in the art as an edge card connector or a clam shell connector. Terminal connector 60 typically includes a plurality of electrical terminals with each having a corresponding electrical wire connected thereto. For the purpose of illustration only, sensors 10 and 10' of FIGS. 1 and 2 are shown having a pair of electrical terminals 100 and 102, which are adapted to be connected to electrical wires 130 and 132 in a known manner. Electrical wires 130 and 132 pass through cable seal 140 which generally comprises a thermoplastic or a thermoset material suitable for use in a high temperature environment, e.g., spark ignition engine. Cable seal 140 is maintained in place by upper shield 20 which has an upper end 23 forming a seat around a shoulder 142 of cable seal 140, wherein upper shield 20 is crimped in place around cable seal 140 to further secure the same. A central portion 24 of upper shield 20 is disposed around terminal connector 60 and a lower end 22 of upper shield 20 forms a cylindrical opening tightly fit around closed first end 42 of inner shield 40 when sensor 10 is assembled. Lower end 22 preferably is held in place by either a tight friction fit or a weld. Preferably, lower end 22 of upper shield 20 has an increased diameter than upper end 23 of upper shield 20 so that it may receive closed first end 42 of inner shield 40, whereby upper shield 20 is preferably secured in a leak-proof manner to closed first end 42 of inner shield 40. Lower end 22 may be secured to closed first end 42 by crimping lower end 22 thereto, as is known in the art, and a crimped portion 28 of lower end 22 will result from such crimping action, as is shown in FIG. 1. It being understood, that when upper shield 20 is crimped to inner shield 40, crimped portion 28 will annularly extend around an outer surface 45 of upper shield 20 and for purposes of illustration only the cross-sectional views of FIGS. 1 and 2 show an uncrimped portion opposite crimped portion 28.

For the structures shown in FIGS. 1 and 2, example material for the shields 20, 30, 40, and 35 and for the shell 50 is high chrome or high nickel stainless steel, all steels chosen for high temperature endurance, high-strength and corrosion resistance. Terminal connector 60 may be formed of a thermoplastic or thermoset material (e.g., plastic) or ceramic durable in the high temperature environments to which exhaust constituent sensor 10 is exposed.

It is within the scope of this invention that high temperature mat support 90 may be made into a more rigid perform, such as with the pair of inner thermal insulating members 120 either being already molded into high temperature mat support 90 or as separate articles. The use of a single or two piece, more rigid perform advantageously eliminates the process of concentrically disposing high temperate mat support 90 around at least a portion of the pair of inner thermal insulating members 120. A perform of the mat material provides a more rigid article and in the case of high temperature mat support 90, the perform provides a structural member which is easily disposed within inner shield 40 to securely hold planar sensing element 80 in place. The manufacture of the perform formed of the mat material may be according to known methods in the relevant arts.

Now turning to FIG. 2, a second exemplary embodiment of the present invention is generally designated as 10'. High temperature mat support 90 extends from closed first end 42 to open second end 44 and extends between planar sensing element 80 and inner surface 41 of inner shield 40. Thus, the use of the pair of inner thermal insulating members 120 is eliminated in this embodiment by strengthening high temperature mat support 90 so that it provides the desired support, strength, and thermal and electrical insulating properties required for sensor 10' to effectively operate in the exhaust system. High temperature mat support 90 may be strengthened by known methods, including but not limited to increasing the binder content of high temperature mat support 90, adding additional binders, or by further compressing high temperature mat support 90.

As shown in FIG. 2, the perform of high temperature mat support 90 includes a central opening for receiving planar sensing element 80 when high temperature mat support 90 is concentrically disposed around at least a portion of planar sensing element 80. It is also within the scope of the invention that high temperature mat support 90 may be used in sensor 10' of FIG. 2 in the non perform state, wherein high temperature mat support 90 is concentrically wrapped around at least a portion of planar sensing element 80 prior to disposing both within inner shield 40.

Sensors 10 and 10' may be constructed according to methods known in the art, including but not limited to using crimping means to securely couple the outer components thereof. When crimping means are used, upper shield 20 is securely coupled to first end 42 of inner shield 40 so that end 84 of planar sensing element 80 is received within upper shield 20 and more particularly between terminals 100 and 102 to provide electrical connection between terminals 100 and 102 and planar sensing element 80. Lower shield 30 is securely coupled to shell 50 by engaging flared open end 32 of lower shield 30 with annular recess 57. Shell 50 is itself securely coupled to inner shield 40 by crimping shell 50 thereto, whereby first end 82 of planar sensing element 80 is disposed within sensing chamber 31 to permit contact with and sensing of exhaust gas.

Thus in accordance with the present invention, planar sensing element 80 is securely held in place within the exhaust constituent sensor of the present invention by disposing a protective high temperature mat support 90 in either a perform or fibrous blanket type state around at least a portion of planar sensing element 80. High temperature protective mat support 90 is intended to concentrically surround at least a portion of planar sensing element 80 to protect planar sensing element 80 and hold the same in place within sensor 10 or 10'. The packaging methods of the present invention offer several advantages over conventional methods of packaging planar sensing element 80 within an exhaust constituent sensor. First, sensors 10 and 10' of the present invention are of a much more simpler design which reduces the manufacturing process by eliminating time consuming steps. As a result, the present invention offers a more cost effective packaging process, while maintaining the desired and necessary structural, thermal, and electrical characteristics described hereinbefore. Furthermore, because the pair of inner thermal insulating members 120 and high temperature mat support 90 act as a thermal and gas barrier, the overall length of sensors 10 and 10' may be reduced.

Typically, the length of conventional exhaust constituent sensors fall within a limited range because the length had to be such that excessive heat radiating outward from the exhaust system was prevented from contacting the electrical connection at one end of the sensor. Because the sensor of the present invention offers improved thermal dissipation of excessive heat, the length of the sensor may be reduced. This of importance for a number of reasons, including that it represents a reduction in costs and it permits the sensor to be mounted in locations which were otherwise not accessible because of the length of the sensor. Alternatively, the length of sensor 10 or 10' may be maintained at a conventional length; however, because of the improvements of the present invention noted herein, sensor 10 or 10' may be used in an environment having higher temperatures. This provides greater versatility in positioning and mounting sensor 10 or 10' within the exhaust system.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. An exhaust constituent sensor, comprising:
    a planar sensing clement having a first end for connecting with at least one electrical terminal, a second and opposite end for contacting exhaust gas, and a central portion extending therebetween;
    a tubular shield within which at least a portion of said planar sensing element extends;
    a high temperature mat support disposed between sad tubular shield and said planar sensing element and about said central portion of said planar sensing element, wherein said high temperature mat support comprises fibrous material and vermiculite; and
    a shell disposed about said tubular shield for mounting said tubular shield to a conduit.

2. The exhaust constituent sensor as set forth in claim 1 wherein said high temperature mat support is concentrically disposed around at least said central portion of said planar sensing element.

3. The exhaust constituent sensor as set forth in claim 1 wherein said high temperature mat support extends between and contacts both said planar sensing element and an inner surface of said tubular shield.

4. The exhaust constituent sensor as set forth in claim 1 wherein said high temperature mat support comprises:
    a ceramic fibrous mat.

5. The exhaust constituent sensor as set forth in claim 4 wherein said ceramic fibrous mat comprises:
    alumina fibers, silica fibers, or a mixture thereof.

6. The exhaust constituent sensor as set forth in claim 1 wherein said high temperature mat support is in the form of a rigid perform, said perform structure having an outer surface for contacting and seating against an inner surface of said tubular shield, and wherein said perform structure includes a central opening through which said planar sensing element passes.

7. The exhaust constituent sensor as set forth in claim 6 wherein a thermal insulating support member is disposed between said perform structure and said planar sensing element, said thermal insulating support member being formed of steatite, alumina, or a ceramic material.

8. The exhaust constituent sensor as set forth in claims 7 wherein said thermal insulating support member comprises:
    a pair of semi-circular ceramic support members, each member having a planar inner surface and an arcuate outer surface, said planar inner surface contacting a planar surface of said planar sensing element and said arcuate outer surface for contacting said perform structure.

9. The exhaust constituent sensor as set forth in claim 1 further comprising:
    a thermal insulating support member disposed between said high temperate mat support and said planar sensing element, wherein said thermal insulating support member contacts at least a portion of said planer sensing element.

10. The exhaust constituent sensor as set forth in claim 9 wherein said thermal insulating support member comprises a pair of a semi-circular support members disposed on first and second planar surfaces of said planar sensing element.

11. The exhaust constituent sensor as set forth in claim 9 wherein said thermal insulating support member is formed of steatite, alumina, or a ceramic material.

12. The exhaust sensor as set forth in claim 1 wherein said high temperature mat support is strengthened by adding a binder or by further compressing said high temperature mat support.

13. The exhaust constituent sensor as set forth in claim 1 wherein said fibrous material comprises a flexible fibrous blanket material.

14. A method for producing an exhaust constituent sensor, comprising:
    disposing a high temperature mat support about at least a central portion of a planar sensing element, said high temperature mat support securely holding said planar sensing element within said sensor, wherein said high temperature mat support comprises fibrous material and vermiculite, and wherein said planar sensing element has a first end for connection with at least one electrical terminal and am opposite second end for contacting exhaust gas; and
    disposing said high temperature mat support and said planar sensing element within a tubular shield wit which at least said central portion of said planar sensing element extends.

15. The method as set forth in claim 14 further comprising:
    wrapping said high temperature mat support around at least said central portion of said planar sensing element, wherein said high temperature mat support contacts at least said central portion of said plan sensing clement.

16. The method as set forth in claim 15 further comprising:
    disposing a thermal insulating support member between said planar sensing element and said high temperature mat support.

17. The method as sot forth in claim 16 wherein said thermal insulating support member comprises first and second semi-circular thermal insulating members, said first semi-circular thermal insulting member contacting a first planar surface of said planar sensing element and said second semi-circular thermal insulating member contacting an opposing second planar surface of said planar sensing element.

18. The method as set forth in claims 14 wherein said high temperature mat support and a thermal insulating support member are in the form of a rigid perform structure, wherein said perform structure includes an opening through which said planar sensing clement passes, said perform structure having an outer surface for contacting and seating against an inner surface of said tubular shield when said perform structure is disposed within said tubular shield.

19. The method as set forth in claim 18 wherein said thermal insulating support member includes first and second semicircular thermal insulating members between said high temperature support and said planar sensing element, said first and second semi-circular thermal insulating members each including a planar inner surface for seating against said planar sensing element and an outer arcuate surface for seating against an inner arcuate surface of said perform structure.

20. An exhaust constituent sensor, comprising:
    a sensing element having a first end for connecting with at least one electrical terminal, a second and opposite end for contacting exhaust gas, and a central portion extending therebetween;
    a tabular shield within which at least a portion of said planar sensing element extends;
    a high temperature mat support disposed between said tubular shield and said planar sensing element and about said central portion of said planar sensing element, wherein said high temperate mat support comprises fibrous material and vermiculite;
    a thermal insulating support member disposed between said high temperature mat support and said sensing element; and
    a shell disposed about said tubular shield for mounting said tubular shield to a conduit.

21. The exhaust constituent sensor as set forth in claim 20, wherein said thermal insulating support member is in physical contact with said sensing element and said high temperature mat support.

22. The exhaust constituent sensor as set forth in claim 21, wherein said high temperature flexible mat support is in physical contact with said tubular shield.

23. The exhaust constituent sensor as set forth in claim 20, wherein said high temperature mat support and said thermal insulating support member are in the form of a rigid perform structure, wherein said perform structure includes an opening through which said planar sensing element passes.

* * * * *